(12) United States Patent
Schaefer et al.

(10) Patent No.: US 7,331,974 B2
(45) Date of Patent: *Feb. 19, 2008

(54) MICROCOIL VASO-OCCLUSIVE DEVICE WITH MULTI-AXIS SECONDARY CONFIGURATION

(75) Inventors: Dean Schaefer, Laguna Hills, CA (US); Horacio Almazan, Rancho Santa Margarita, CA (US); David A. Ferrera, Manhattan Beach, CA (US); Brian J. Cox, Laguna Niguel, CA (US); George R. Greene, Jr., Costa Mesa, CA (US)

(73) Assignee: Microvention, Inc., Aliso Viejo, CA (US)

( * ) Notice: Subject to any disclaimer, the term of this patent is extended or adjusted under 35 U.S.C. 154(b) by 88 days.

This patent is subject to a terminal disclaimer.

(21) Appl. No.: 10/638,813

(22) Filed: Aug. 11, 2003

(65) Prior Publication Data

US 2004/0045554 A1 Mar. 11, 2004

Related U.S. Application Data

(63) Continuation of application No. 09/671,021, filed on Sep. 26, 2000, now Pat. No. 6,605,101.

(51) Int. Cl.
*A61M 29/00* (2006.01)
(52) U.S. Cl. .................................... 606/200
(58) Field of Classification Search ............. 606/108, 606/191, 198, 151, 157, 158, 200, 194
See application file for complete search history.

(56) References Cited

U.S. PATENT DOCUMENTS 4,551,132 A 11/1985 Pasztor et al.

(Continued)

FOREIGN PATENT DOCUMENTS

DE 19647280 10/1997

(Continued)

OTHER PUBLICATIONS

Gianturco, M.D. et al.; "Mechanical Devices for Arterial Occlusion" Jul. 1975, vol. 124, No. 3., pp. 428-435.

(Continued)

*Primary Examiner*—Kevin T. Truong
(74) *Attorney, Agent, or Firm*—Inskeep IP Group, Inc.

(57) ABSTRACT

A vaso-occlusive device includes a microcoil formed into a minimum energy state secondary configuration comprising a plurality of curved segments, each defining a discrete axis, whereby the device, in its minimum energy state configuration, defines multiple axes. In a preferred embodiment, the minimum energy state secondary configuration comprises a plurality of tangentially-interconnected, substantially circular loops defining a plurality of discrete axes. In an alternative embodiment, the minimum energy state secondary configuration defines a wave-form like structure comprising a longitudinal array of laterally-alternating open loops defining a plurality of separate axes. In either embodiment, the device, in its minimum energy state secondary configuration, has a dimension that is substantially larger than the largest dimension of the vascular site in which the device is to be deployed. Thus, when the device is deployed in an aneurysm, the confinement of the device within the aneurysm causes the device to assume a three-dimensional configuration that has a higher energy state than the minimum energy state. Because the minimum energy state of the device is larger (in at least one dimension) than the aneurysm, the deployed device is constrained by its intimate contact with the walls of the aneurysm from returning to its minimum energy state configuration. Therefore, the device still engages the surrounding aneurysm wall surface, thereby minimizing shifting or tumbling due to blood flow dynamics. Furthermore, the minimum energy state secondary configuration (to which the device attempts to revert) is not one that is conducive to "coin stacking", thereby minimizing the degree of compaction that is experienced.

18 Claims, 3 Drawing Sheets

U.S. PATENT DOCUMENTS

| | | |
|---|---|---|
| 4,795,741 A | 1/1989 | Leshchiner et al. |
| 4,819,637 A | 4/1989 | Dormandy, Jr. et al. |
| 4,994,069 A | 2/1991 | Ritchart et al. |
| 5,108,407 A | 4/1992 | Geremia et al. |
| 5,122,136 A | 6/1992 | Guglielmi et al. |
| 5,133,731 A | 7/1992 | Butler et al. |
| 5,226,911 A | 7/1993 | Chee et al. |
| 5,234,437 A | 8/1993 | Sepetka |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,350,397 A | 9/1994 | Palermo et al. |
| 5,382,259 A | 1/1995 | Phelps et al. |
| 5,382,260 A | 1/1995 | Dormandy, Jr. et al. |
| 5,423,829 A | 6/1995 | Pham et al. |
| 5,476,472 A | 12/1995 | Dormandy, Jr. et al. |
| 5,522,836 A | 6/1996 | Palermo |
| 5,525,334 A | 6/1996 | Ito et al. |
| 5,527,338 A | 6/1996 | Purdy |
| 5,536,274 A | 7/1996 | Neuss |
| 5,578,074 A | 11/1996 | Mirigian |
| 5,580,568 A | 12/1996 | Greff et al. |
| 5,582,619 A * | 12/1996 | Ken .......................... 606/191 |
| 5,624,461 A | 4/1997 | Mariant |
| 5,639,277 A | 6/1997 | Mariant et al. |
| 5,645,558 A | 7/1997 | Horton |
| 5,645,564 A | 7/1997 | Northrup et al. |
| 5,649,949 A | 7/1997 | Wallace et al. |
| 5,658,308 A | 8/1997 | Snyder |
| 5,690,667 A | 11/1997 | Gia |
| 5,690,671 A | 11/1997 | McGurk et al. |
| 5,700,258 A | 12/1997 | Mirigian et al. |
| 5,718,711 A | 2/1998 | Berenstein et al. |
| 5,725,546 A | 3/1998 | Samson |
| 5,749,891 A | 5/1998 | Ken et al. |
| 5,797,953 A | 8/1998 | Tekulve |
| 5,814,062 A | 9/1998 | Sepetka et al. |
| 5,868,754 A * | 2/1999 | Levine et al. ................ 606/108 |
| D407,818 S | 4/1999 | Mariant |
| 5,891,058 A | 4/1999 | Taki et al. |
| 5,911,731 A | 6/1999 | Pham et al. |
| 5,911,737 A | 6/1999 | Lee et al. |
| 5,957,948 A | 9/1999 | Mariant |
| 5,980,514 A * | 11/1999 | Kupiecki et al. ........... 606/108 |
| 5,989,242 A | 11/1999 | Saadat et al. |
| 6,013,084 A | 1/2000 | Ken et al. |
| 6,015,424 A | 1/2000 | Rosenbluth et al. |
| D421,304 S | 2/2000 | Mariant et al. |
| 6,022,369 A | 2/2000 | Jacobsen et al. |
| 6,024,765 A | 2/2000 | Wallace et al. |
| 6,063,100 A | 5/2000 | Diaz et al. |
| D427,680 S | 7/2000 | Mariant et al. |
| 6,102,933 A | 8/2000 | Lee et al. |
| 6,176,240 B1 * | 1/2001 | Nikolchev et al. .......... 128/830 |
| RE37,117 E * | 3/2001 | Palermo ........................ 606/1 |
| 6,280,457 B1 | 8/2001 | Wallace et al. |
| 6,322,576 B1 | 11/2001 | Wallace et al. |
| 2002/0107534 A1 | 8/2002 | Schaefer et al. |
| 2003/0120302 A1 | 6/2003 | Minck, Jr. et al. |

FOREIGN PATENT DOCUMENTS

| | | |
|---|---|---|
| EP | 0 739 605 | 4/1996 |
| WO | WO 94/11051 | 5/1994 |
| WO | WO 98/02100 | 1/1998 |
| WO | WO 98/17183 | 4/1998 |
| WO | WO 99/09893 | 3/1999 |
| WO | WO 00/21443 | 4/2000 |
| WO | WO 00/74577 | 12/2000 |
| WO | WO 01/45571 | 6/2001 |
| WO | WO 01/93780 | 12/2001 |
| WO | WO 02/32325 | 4/2002 |

OTHER PUBLICATIONS

Anderson, James et al.; "Transcatheter Intravascular Coil Occlusion . . . " American Journal Roentgennol 129:795-798, Nov. 1977.

Anderson, James et al.; "Mini Gianturco Stainless Steel Coils for Transcatheter Vascular Occlusion" Radiology 132:301-303, Aug. 1979.

Lund, Gunnar et al.; "Detachable Steel Spring Coils for Vessel Occlusion" Radiology 1985; 155-530.

Malek, Adel M. et al.; "Treatment of an Intracranial Aneursym Using a New . . . " Neurosurgery, vol. 44, No. 5, May 1999.

Tan, C. B. et al.; "The Feasibility of Three-Dimensional Guglielmi Detachable Coil for Embolisation of Wide Neck Cerebral Aneurysms" Interventional Neuroradiology 6: 53-57, 2000.

Cloft, Harry J. et al.; "Use of Three-dimensional Guglielmi Detachable Coils . . . " AJNR AM J. Neuroradiol 21:1312-1314 Aug. 2000.

* cited by examiner

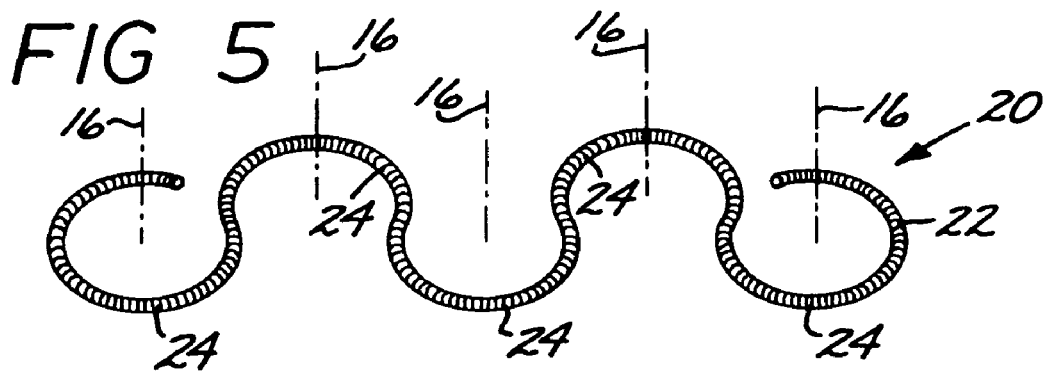
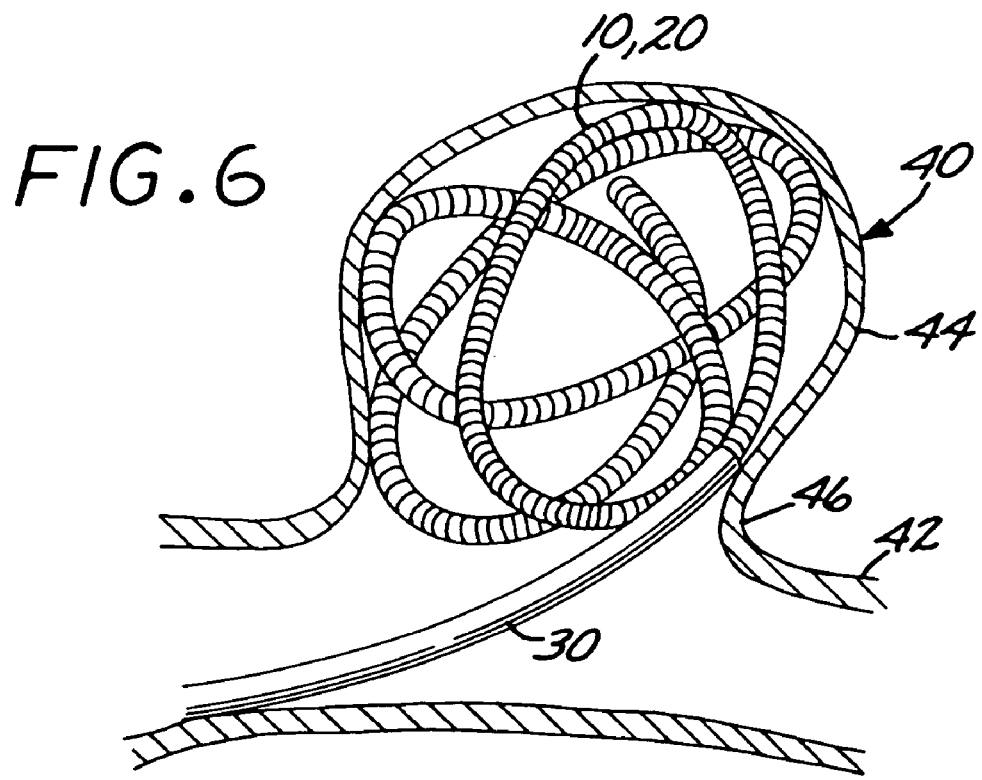

MICROCOIL VASO-OCCLUSIVE DEVICE WITH MULTI-AXIS SECONDARY CONFIGURATION

CROSS-REFERENCE TO RELATED APPLICATIONS

This application is a continuation of U.S. application Ser. No. 09/671,021; filed Sep. 26, 2000 now U.S. Pat. No. 6,605,101.

FEDERALLY-SPONSORED RESEARCH OR DEVELOPMENT

Not Applicable

BACKGROUND OF THE INVENTION

This invention relates generally to the field of vascular occlusion devices and methods. More specifically, it relates to an apparatus and method for occluding a blood vessel by embolizing a targeted site (such as an aneurysm) in the blood vessel.

The embolization of blood vessels is desired in a number of clinical situations. For example, vascular embolization has been used to control vascular bleeding, to occlude the blood supply to tumors, and to occlude vascular aneurysms, particularly intracranial aneurysms. In recent years, vascular embolization for the treatment of aneurysms has received much attention. Several different treatment modalities have been employed in the prior art. U.S. Pat. No. 4,819,637—Dormandy, Jr. et al., for example, describes a vascular embolization system that employs a detachable balloon delivered to the aneurysm site by an intravascular catheter. The balloon is carried into the aneurysm at the tip of the catheter, and it is inflated inside the aneurysm with a solidifying fluid (typically a polymerizable resin or gel) to occlude the aneurysm. The balloon is then detached from the catheter by gentle traction on the catheter. While the balloon-type embolization device can provide an effective occlusion of many types of aneurysms, it is difficult to retrieve or move after the solidifying fluid sets, and it is difficult to visualize unless it is filled with a contrast material. Furthermore, there are risks of balloon rupture during inflation and of premature detachment of the balloon from the catheter.

Another approach is the direct injection of a liquid polymer embolic agent into the vascular site to be occluded. One type of liquid polymer used in the direct injection technique is a rapidly polymerizing liquid, such as a cyanoacrylate resin, particularly isobutyl cyanoacrylate, that is delivered to the target site as a liquid, and then is polymerized in situ. Alternatively, a liquid polymer that is precipitated at the target site from a carrier solution has been used. An example of this type of embolic agent is a cellulose acetate polymer mixed with bismuth trioxide and dissolved in dimethyl sulfoxide (DMSO). Another type is ethylene glycol copolymer dissolved in DMSO. On contact with blood, the DMSO diffuses out, and the polymer precipitates out and rapidly hardens into an embolic mass that conforms to the shape of the aneurysm. Other examples of materials used in this "direct injection" method are disclosed in the following U.S. Pat. No. 4,551,132—Pasztor et al.; U.S. Pat. No. 4,795,741—Leshchiner et al.; U.S. Pat. No. 5,525,334—Ito et al.; and U.S. Pat. No. 5,580,568—Greffet al.

The direct injection of liquid polymer embolic agents has proven difficult in practice. For example, migration of the polymeric material from the aneurysm and into the adjacent blood vessel has presented a problem. In addition, visualization of the embolization material requires that a contrasting agent be mixed with it, and selecting embolization materials and contrasting agents that are mutually compatible may result in performance compromises that are less than optimal. Furthermore, precise control of the deployment of the polymeric embolization material is difficult, leading to the risk of improper placement and/or premature solidification of the material. Moreover, once the embolization material is deployed and solidified, it is difficult to move or retrieve.

Another approach that has shown promise is the use of thrombogenic microcoils. These microcoils may be made of a biocompatible metal alloy (typically platinum and tungsten) or a suitable polymer. If made of metal, the coil may be provided with Dacron fibers to increase thrombogenicity. The coil is deployed through a microcatheter to the vascular site. Examples of microcoils are disclosed in the following U.S. Pat. No.: 4,994,069—Ritchart et al.; U.S. Pat. No. 5,122,136—Guglielmi et al.; U.S. Pat. No. 5,133,731—Butler et al.; U.S. Pat. No. 5,226,911—Chee et al.; U.S. Pat. No. 5,304,194—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,639,277—Mariant et al.; U.S. Pat. No. 5,658,308—Snyder; U.S. Pat. No. 5,690,667—Gia; U.S. Pat. No. 5,690,671—McGurk et al.; U.S. Pat. No. 5,700,258—Mirigian et al.; U.S. Pat. No. 5,718,711—Berenstein et al.; U.S. Pat. No. 5,891,058—Taki et al.; U.S. Pat. No. 6,013,084—Ken et al.; U.S. Pat. No. 6,015,424—Rosenbluth et al.; and Des. U.S. Pat. No. 427,680—Mariant et al.

While many prior art microcoil devices have met with some success in treating small aneurysms with relatively narrow necks, it has been recognized that the most commonly used microcoil vaso-occlusive devices achieve less than satisfactory results in wide-necked aneurysms, particularly in the cerebrum. This has led to the development of three-dimensional microcoil devices, such as those disclosed in U.S. Pat. No. 5,645,558—Horton; U.S. Pat. No. 5,911,731—Pham et al.; and U.S. Pat. No. 5,957,948—Mariant (the latter two being in a class of devices known as "three-dimensional Guglielmi detachable coils", or "3D-GDC's"). See, e.g., Tan et al., "The Feasibility of Three-Dimensional Guglielmi Detachable Coil for Embolisation of Wide Neck Cerebral Aneurysms," *Interventional Neuroradiology*, Vol. 6, pp. 53-57 (June, 2000); Cloft et al., "Use of Three-Dimensional Guglielmi Detachable Coils in the Treatment of Wide-necked Cerebral Aneurysms," *American Journal of Neuroradiology*, Vol. 21, pp. 1312-1314 (August, 2000).

The typical three-dimensional microcoil is formed from a length of wire that is formed first into a primary configuration of a helical coil, and then into a secondary configuration that is one of a variety of three-dimensional shapes. The minimum energy state of this type of microcoil is its three-dimensional secondary configuration. When deployed inside an aneurysm, these devices assume a three-dimensional configuration, typically a somewhat spherical configuration, that is at or slightly greater than, the minimum energy state of the secondary configuration. Because the overall dimensions of these devices in their non-minimum energy state configuration is approximately equal to or smaller than the interior dimensions of the aneurysm, there is nothing to constrain the device from shifting or tumbling within the aneurysm due to blood flow dynamics.

In some of these three-dimensional devices (e.g., U.S. Pat. No. 5,122,136—Guglielmi et al.), the secondary configuration is itself a helix or some similar form that defines a longitudinal axis. Devices with what may be termed a "longitudinal" secondary configuration form a three-dimensional non-minimum energy state configuration when deployed inside an aneurysm, but, once deployed, they have displayed a tendency to revert to their minimum energy state configurations. This, in turn, results in compaction due to "coin stacking" (i.e., returning to the secondary helical configuration), thereby allowing recanalization of the aneurysm.

There has thus been a long-felt, but as yet unsatisfied need for a microcoil vaso-occlusive device that has the advantages of many of the prior art microcoil devices, but that can be used effectively to treat aneurysms of many different sizes configurations, and in particular those with large neck widths. It would be advantageous for such a device to be compatible for use with existing guidewire and microcatheter microcoil delivery mechanisms, and to be capable of being manufactured at costs comparable with those of prior art microcoil devices.

SUMMARY OF THE INVENTION

Broadly, the present invention is a microcoil vaso-occlusive device that has a minimum energy state secondary configuration comprising a plurality of curved segments, each defining a discrete axis, whereby the device, in its minimum energy state configuration, defines multiple axes. More specifically, each segment defines a plane and an axis that is substantially perpendicular to the plane.

In a particular preferred embodiment, the present invention is an elongate microcoil structure having a minimum energy state secondary configuration that defines a plurality of tangentially-interconnected, substantially circular loops defining a plurality of separate axes. In one form of the preferred embodiment, the substantially circular closed loops are substantially coplanar and define axes that are substantially parallel. That is, the planes defined by the segments are themselves substantially coplanar. In another form of the preferred embodiment, each pair of adjacent loops defines a shallow angle, whereby their respective axes define an angle of not more than about 90°, and preferably not more than about 45°, between them.

In an alternative embodiment, the microcoil structure has a minimum energy state secondary configuration that defines a wave-form like structure comprising a longitudinal array of laterally-alternating open loops defining a plurality of separate axes. As in the preferred embodiment, the alternative embodiment may be in a first form in which the loops are substantially coplanar and their respective axes are substantially parallel, or in a second form in which each pair of adjacent loops defines a shallow angle, whereby their respective axes define an angle of not more than about 90°, and preferably not more than about 45°, between them.

In either embodiment, the device, in its minimum energy state secondary configuration, has a dimension that is substantially larger (preferably at least about 25% greater) than the largest dimension of the vascular space in which the device is to be deployed. Thus, when the device is deployed inside a vascular site such as an aneurysm, the confinement of the device within the site causes the device to assume a three-dimensional configuration that has a higher energy state than the minimum energy state. Because the minimum energy state of the device is larger (in at least one dimension) than the space in which it is deployed, the deployed device is constrained by its intimate contact with the walls of the aneurysm from returning to its minimum energy state configuration. Therefore, the device still engages the surrounding aneurysm wall surface, thereby minimizing shifting or tumbling due to blood flow dynamics. Furthermore, the minimum energy state secondary configuration (to which the device attempts to revert) is not one that is conducive to "coin stacking", thereby minimizing the degree of compaction that is experienced.

As will be better appreciated from the detailed description that follows, the present invention provides for effective embolization of vascular structures (particularly aneurysms) having a wide variety of shapes and sizes. It is especially advantageous for use in wide-necked aneurysms. Furthermore, as will be described in more detail below, the present invention may be deployed using conventional deployment mechanisms, such as microcatheters and guidewires.

BRIEF DESCRIPTION OF THE DRAWINGS

FIG. 5 is a plan view of a microcoil vaso-occlusive device in accordance with an alternative embodiment of the invention;

FIG. 6 is an elevational view of the present invention in the process of being deployed through a microcatheter into a wide-necked aneurysm.

DETAILED DESCRIPTION OF THE INVENTION

Figure 1:
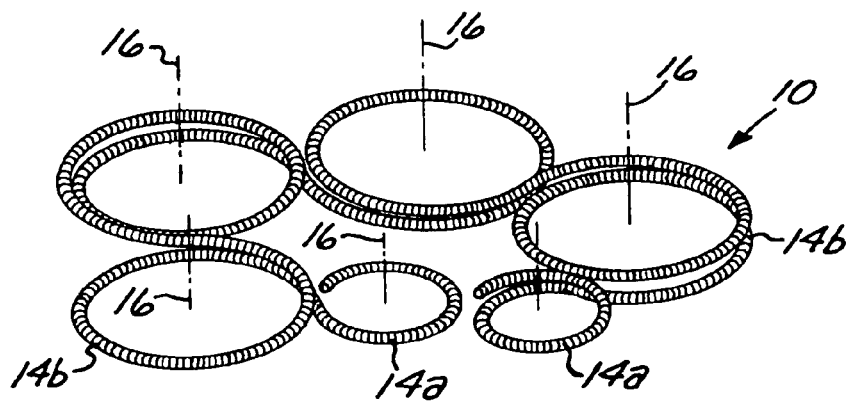
FIG. 1 is a perspective view of a microcoil vaso-occlusive device in accordance with a preferred embodiment of the present invention.
Figure 2:
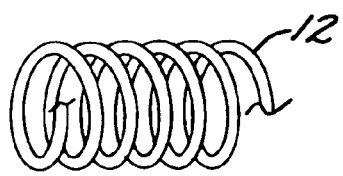
FIG. 2 is a partial view of the device of FIG. 1, taken within the area designated by the numeral 2 in FIG. 1.
Figure 3:
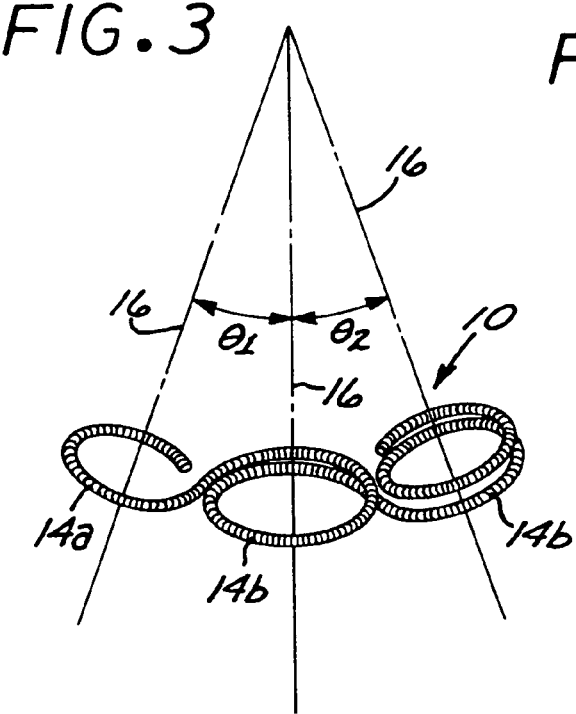
FIGS. 3 and 4 are partial views of a microcoil vaso-occlusive device in accordance with another form of the preferred embodiment of the present invention.
Figure 4:
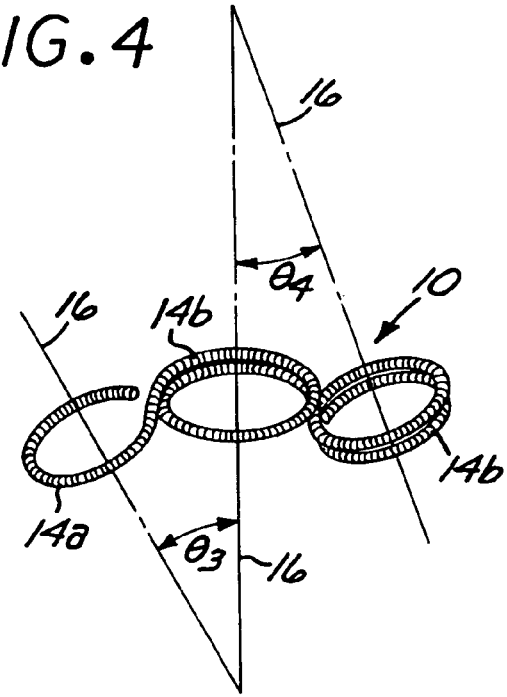

Referring first to FIGS. 1-4 and 6, a microcoil vaso-occlusive device 10, in accordance with a preferred embodiment of the invention is shown. The device 10 comprises a suitable length of wire formed into the primary configuration of a helical microcoil 12 (FIG. 2). Suitable materials for the device 10 include platinum, rhodium, palladium, rhenium, tungsten, gold, silver, tantalum, and various alloys of these metals. Various surgical grade stainless steels may also be used. Preferred materials include the platinum/tungsten alloy known as Platinum 479 (92% Pt, 8% W, available from Sigmund Cohn, of Mount Vernon, N.Y.) and titanium/nickel alloys (such as the titanium/nickel alloy known as "nitinol"). Another material that may be advantageous is a bimetallic wire comprising a highly elastic metal with a highly radiopaque metal. Such a bimetallic wire would also be resistant to permanent deformation. An example of such a bimetallic wire is a product comprising a nitinol outer layer and an inner core of pure reference grade platinum, available from Sigmund Cohn, of Mount Vernon, N.Y., and Anomet Products, of Shrewsbury, Mass. Wire diameters of about 0.0125 mm to about 0.150 mm may be used.

The microcoil 12 has a diameter that is typically in the range of about 0.125 mm to about 0.625 mm, with a preferred range, for most neurovascular applications, of about 0.25 mm to about 0.40 mm. The axial length of the microcoil 12 may be anywhere from about 5 mm to about 1000 mm, with about 20 mm to about 400 mm being typical.

The primary winding of the microcoil 12 is applied under tension. The amount of tension, and the pitch of the primary winding, determine the stiffness of the microcoil 12. These parameters can be varied along the length of the microcoil 12 to form a microcoil having different degrees of stiffness along its length, which may be advantageous in certain applications.

The microcoil 12 is formed into a secondary configuration that comprises a plurality of curved segments, each defining an axis, whereby the microcoil 12 defines multiple axes. More specifically, each of the curved segments defines a plane and an axis that is substantially perpendicular to the plane. In the preferred embodiment of FIGS. 1-4, the curved segments are tangentially-interconnected, substantially circular loops 14a, 14b defining a plurality of separate axes 16. In one form of the preferred embodiment, shown in FIG. 1, the substantially circular loops 14a, 14b are substantially coplanar and define axes 16 that are substantially parallel. In another form of the preferred embodiment, shown in FIGS. 3 and 4, each pair of adjacent loops 14a, 14b defines a shallow angle, whereby their respective axes 16 define an angle (θ1, θ2, θ3, and θ4) of not more than about 90° between them, and preferably not more than about 45°.

The preferred embodiment of the invention typically includes a pair of end loops 14a and at least one intermediate loop 14b. Typically, there will be up to four intermediate loops 14b, depending on the vascular site to be embolized, but there may be as many as six or more, for use in very large vascular sites. The intermediate loops are sized to have a diameter approximately equal to the maximum diameter of the target vascular site (e.g., an aneurysm), while the end loops 14a have a slightly smaller diameter (preferably, approximately 1.5 mm smaller), for purposes to be described below.

The primary microcoil 12 is formed into the secondary configuration by heat treatment, as is well known in the art. For example, the annealed primary coil may be initially placed into the secondary configuration by winding or wrapping around a suitably shaped and sized mandrel of refractory material, and then subjected to an annealing temperature for a specified period of time. For Platinum 479, for example, an annealing temperature of about 500° C. to about 1000° C., preferably approximately 670° C., is maintained for about 30 to 90 minutes, preferably about 60 minutes, then cooled to room temperature and ultrasonically cleaned. The resultant secondary configuration is thereby made permanent, and it becomes the minimum energy state configuration of the microcoil 12.

Figure 7:
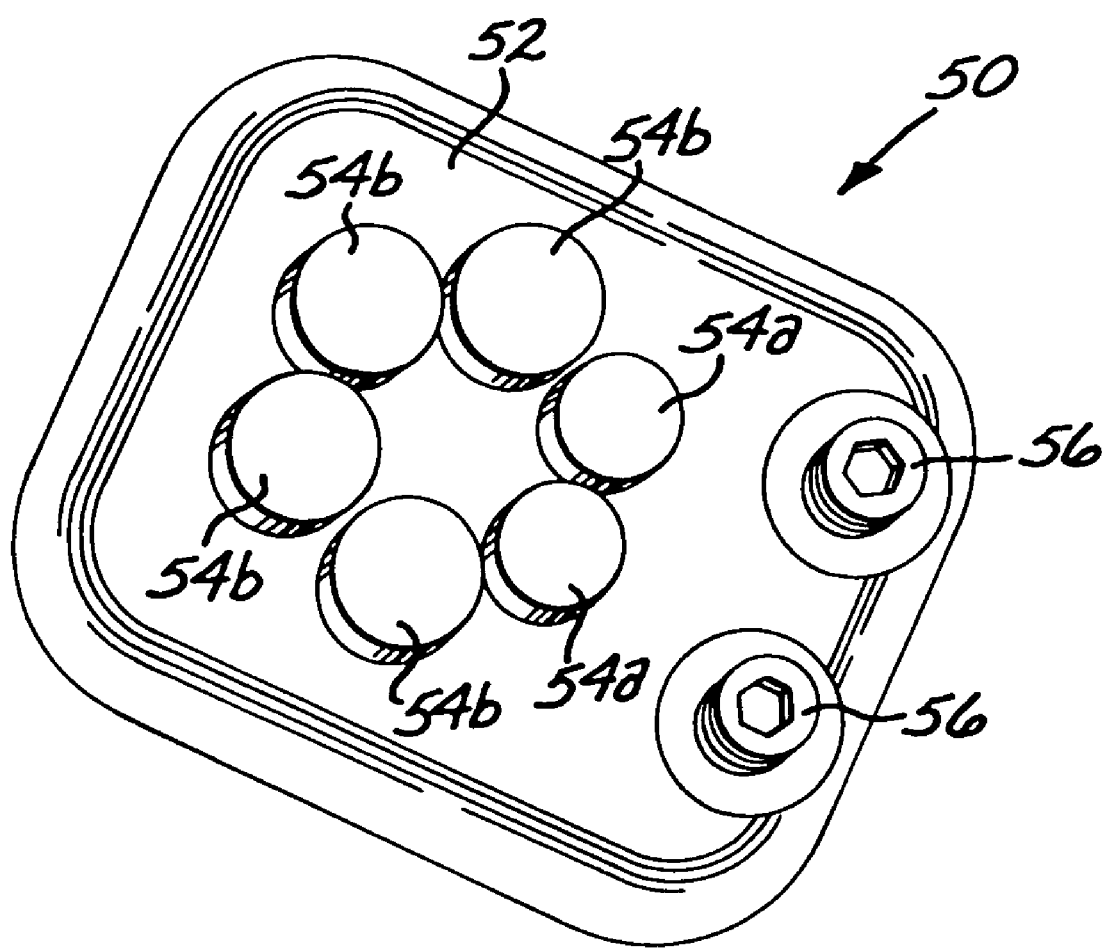
FIG. 7 is a perspective view of a heat treatment fixture used to manufacture the preferred embodiment of the present invention.

FIG. 7 shows a heat treatment fixture 50 used in the manufacture of the preferred embodiment of the invention. The fixture 50 is made of a refractory material, and it includes a base 52 having a surface on which is provided a mandrel for the secondary winding. The mandrel comprises a plurality of winding pins 54a, 54b extending upwardly from the surface of the base 52. The exemplary fixture 50 shown in the drawing has six pins arranged in roughly a hexagonal pattern. There are two end winding pins 54a adjacent each other, and four intermediate winding pins 54b. A pair of fastening pegs 56 is located near one end of the fixture, for fastening the ends of the primary coil 12.

The diameters of the end winding pins 54a are slightly smaller than the diameters of the intermediate winding pins 54b to achieve the size relationships described above. The spacings between the pins 54a, 54b are only slightly greater than the diameter of the primary coil 12, so that only one wind of the primary coil can be passed around the pins with each winding of the secondary coil. Each subsequent winding of the secondary coil is thus stacked on top of the previous winding. This eliminates any straight sections in the secondary coil, which, during deployment, would tend to push the coil into the parent artery.

During the secondary winding process, the primary coil 12 is kept under tension. The amount of tension can be adjusted to control the degree of spring-back of the loops 14a, 14b of the microcoil 12.

The secondary winding of the microcoil 12 is performed so that the loops 14a, 14b reverse direction as the microcoil 12 is wrapped around each successive pin on the fixture. This ensures that loops will not coin stack, and that they will disperse randomly throughout the aneurysm once deployed. Furthermore, in the preferred embodiment, each loop is wound a complete 360° before the next loop is wound. This ensures that each loop will completely seat within the aneurysm before the microcoil 12 reverses direction. With a complete loop intact, the loop strength is maximized, and the loop distributes loads evenly.

FIG. 5 shows a microcoil vaso-occlusion device 20 in accordance with an alternative embodiment of the invention. This embodiment includes a primary microcoil 22 formed into a secondary minimum energy state configuration that defines a wave-form like structure comprising a longitudinal array of laterally-alternating, preferably non-overlapping open loops 24, in which alternate loops extend in laterally opposite directions, the open loops 24 defining a plurality of separate and discrete axes 16. Thus, each loop 24 defines a plane, with a unique axis 16 orthogonal to that plane. As in the preferred embodiment, the alternative embodiment may be in a first form in which the loops 24 are substantially coplanar and their respective axes 16 are substantially parallel, or in a second form in which each pair of adjacent loops 24 defines a shallow angle, whereby their respective axes 16 define an angle of not more than about 90°, and preferably not more than about 45°, between them. The materials, dimensions, and method of manufacture of this alternative embodiment are, in all material respects, similar to those of the preferred embodiment described above.

The method of using the present invention is shown in FIG. 6. In use, the proximal end of the microcoil 12 (or 22) is attached to the distal end of a guidewire or microcatheter (not shown). The attachment may be by any of a number of ways known in the art, as exemplified by the following U.S. patents, the disclosures of which are expressly incorporated herein by reference: U.S. Pat. No. 5,108,407—Geremia et al.; U.S. Pat. No. 5,122,136—Guglielmi et al.; U.S. Pat. No. 5,234,437—Sepetka; U.S. Pat. No. 5,261,916—Engelson; U.S. Pat. No. 5,304,195—Twyford, Jr. et al.; U.S. Pat. No. 5,312,415—Palermo; U.S. Pat. No. 5,423,829—Pham et al.; U.S. Pat. No. 5,522,836—Palermo; U.S. Pat. No. 5,645,564—Northrup et al.; U.S. Pat. No. 5,725,546—Samson; U.S. Pat. No. 5,800,453—Gia; U.S. Pat. No. 5,814,062—Sepetka et al.; U.S. Pat. No. 5,911,737—Lee et al.; U.S. Pat. No. 5,989,242—Saadat et al.; U.S. Pat. No. 6,022,369—Jacobsen et al. U.S. Pat. No. 6,063,100—Diaz et al.; U.S. Pat. No. 6,068,644—Lulo et al.; and U.S. Pat. No. 6,102,933—Lee et al.

A target vascular site is visualized, by conventional means, well-known in the art. The target vascular site may be an aneurysm 40 branching off a parent artery 42. The aneurysm 40 has a dome 44 connected to the branch artery by a neck 46. A catheter 30 is passed intravascularly until it enters the dome 44 of the aneurysm 40 via the neck 46. The microcoil 12 is passed through the catheter 30 with the assistance of the guidewire or microcatheter until the microcoil 12 enters the dome 44 of the aneurysm 40.

The undersized end loop 14a at the distal end of the microcoil 12 enters the aneurysm first. This assists in seating the first loop properly, because the smaller size keeps the first loop inside the neck 46 of the aneurysm, avoiding the parent artery 42.

The intermediate loops 14b then enter the aneurysm. Because they are sized to fit the aneurysm, they can deploy freely and smoothly with minimal friction against the wall of the aneurysm. Because the secondary configuration of the microcoil 12 is essentially coplanar, all of the intermediate loops exert a force against the walls of the aneurysm dome 44, thereby improving the resistance of the microcoil 12 to shifting due to pulsatile blood flow.

As the microcoil 12 enters the aneurysm, it attempts to assume its secondary configuration. Because the microcoil, in its secondary configuration, is larger than the aneurysm, however, it is constrained into a deployed configuration in which it tends to fill the interior volume of the aneurysm. In this deployed configuration, the microcoil is in an energy state that is substantially higher than its minimum energy state. Thus, when the device is deployed inside a vascular site such as an aneurysm, the confinement of the device within the site causes the device to assume a three-dimensional configuration that has a higher energy state than the minimum energy state. Because the minimum energy state of the device is larger (in at least one dimension) than the space in which it is deployed, the deployed device is constrained by its intimate contact with the walls of the aneurysm from returning to its minimum energy state configuration. Therefore, the device still engages the surrounding aneurysm wall surface, thereby minimizing shifting or tumbling due to blood flow dynamics. Furthermore, the minimum energy state secondary configuration (to which the device attempts to revert) is not one that is conducive to "coin stacking", thereby minimizing the degree of compaction that is experienced.

The undersized end loop 14a at the proximal end of the microcoil 12 enters the aneurysm last. After the microcoil is fully deployed, it is controllably detached from the guidewire by any suitable means well-known in the art, thereby allowing the microcatheter or guidewire to be withdrawn, leaving the microcoil in place to embolize the aneurysm. After detachment, the proximal end loop 14a curls into the neck 46 of the aneurysm 40, avoiding the parent artery 42.

The present invention thus exhibits several advantages over prior art three-dimensional microcoils. For example, there is increased coverage of the aneurysm neck, due to the presence of loops across the neck, yet the probability of any part of the device intruding into the parent artery is reduced. The secondary coil configuration also provides smoother deployment, and, once deployed, the device exhibits greater resistance to coil compaction, thereby increasing positional stability in the face of pulsatile blood flow. This stability is achieved with lower overall friction between the device and the aneurysm wall. Moreover, the random distribution of loops throughout the aneurysm allows the device to maintain a complex shape inside the aneurysm, yielding improved embolization.

While a preferred embodiment and an alternative embodiment of the invention have been described herein, it will be appreciated that a number of variations and modifications will suggest themselves to those skilled in the pertinent arts. For example, other secondary configurations than those described herein may be found that will yield most, if not all, of the significant advantages of the invention for treatment of the typical aneurysm, or that will prove especially advantageous in specific clinical applications. Also, for specific applications, the dimensions and materials may be varied from those disclosed herein if found to be advantageous. These and other variations and modifications are considered to be within the spirit and scope of the invention, as defined in the claims that follow.

What is claimed is:

1. A vaso-occlusive device, comprising an elongate, filamentous element that has been pre-formed into a secondary minimum energy state relaxed configuration to which at least a portion of the element reverts when the filamentous element is unconstrained, wherein the secondary minimum energy state configuration is a wave-form configuration comprising a longitudinal array of open loops, wherein alternating loops extend laterally in opposite directions, and wherein each loop defines a plane and a separate and discrete axis orthogonal to that plane.

2. The device of claim 1, wherein substantially the entire filamentous element reverts to a wave-form configuration when the filamentous element is unconstrained.

3. The device of claim 1, wherein the secondary minimum energy state relaxed configuration is a configuration in which a distal portion of the filamentous element has a wave-form configuration.

4. The device of claim 1, wherein the filamentous element has a proximal end that is electrolytically detachable from a delivery device.

5. The device of claim 1, wherein the loops are substantially co-planar and their respective axes are substantially parallel.

6. The device of claim 1, wherein each pair of adjacent loops defines a shallow angle.

7. The device of claim 6, wherein the defined angle is not more than 90°.

8. The device of claim 7, wherein the defined angle is not more than 45°.

9. The device of claim 1, wherein the loops are non-overlapping.

10. The device of claim 1, wherein the filamentous element is a microcoil that has been pre-formed into the secondary minimum energy state relaxed configuration.

11. A method of occluding a vascular site, comprising:
   accessing the vascular site with a delivery apparatus;
   providing a vaso-occlusive device comprising an elongate, filamentous element that has been pre-formed into a secondary minimum energy state relaxed configuration to which at least a portion of the filamentous element reverts when the filamentous element is unconstrained, wherein the secondary minimum energy state configuration is a waveform configuration comprising a longitudinal array of open loops, wherein alternating loops extend laterally in opposite directions, and wherein each loop defines a plane and a separate and discrete axis orthogonal to that plane; and
   deploying the vaso-occlusive device from the delivery apparatus into the vascular site in a maimer allowing a portion of the filamentous element to revert to its relaxed wave-form configuration in the vascular site so as to form an embolizing structure in the vascular site.

12. The method of claim 11, wherein the vascular site is an aneurysm.

13. The method of claim 11, wherein the filamentous element comprises a microcoil that has been into the secondary minimum energy state relaxed configuration.

14. The method of claim 11, wherein the loops of the filamentous element are non-overlapping.

15. The method of claim 11, wherein the loops of the filamentous element are substantially co-planar and their respective axes are substantially parallel.

16. The method of claim 11, wherein each pair of adjacent loops of the filamentous element defines a shallow angle.

17. The method of claim 16, wherein the defined angle is not more than 90°.

18. The method of claim 17, wherein the defined angle is not more than 45°.

* * * * *